United States Patent [19]

Hwang et al.

[11] Patent Number: 5,166,173
[45] Date of Patent: Nov. 24, 1992

[54] METHOD OF TREATING HERPES SIMPLEX VIRUS INFECTION

[75] Inventors: Kou M. Hwang, Danville; You M. Qi, Redwood City; Su-Ying Liu, Belmont, all of Calif.

[73] Assignee: Genelabs Incorporated, Redwood City, Calif.

[21] Appl. No.: 647,469

[22] Filed: Jan. 29, 1991

[51] Int. Cl.$^5$ .................. A01N 33/02; A61K 31/13; A61K 31/21; A61K 31/135

[52] U.S. Cl. ..................... 514/510; 514/553; 514/577; 514/656; 514/660

[58] Field of Search .............. 514/553, 577, 510, 656, 514/660

[56] References Cited

PUBLICATIONS

Akerfeldt, S., et al., J. Med. Chem. 14(7):596-600 (1971).
Hansch, C. and Leo, A. Chapter VI, Table VI-1, in "Substituent Constants for Correlation Analysis in Chemistry and Biology" Wiley, Ed., New York 1979 pp. 48-54.
Poh, B-L and Lim, C. S., Tetrahedron 46, No. 10 (1990) 3651-3658.
Poh, B-L et al., Tetrahedron 46, No. 12, (1990) 4379-4386.
Poh, B-L et al., Tetrahedron 30, No. 8 (1989) 1005-1008.
Merluzzi, V. J. et al., Science 250, (Dec. 7 1989) 1411-1413.

*Primary Examiner*—Nathan M. Nutter
*Attorney, Agent, or Firm*—Peter J. Dehlinger

[57] ABSTRACT

A method of inhibiting cell infection by herpes simplex virus-1 or -2. The method includes contacting the virus with a macrocyclic chromotropic acid compound, in an amount effective to inhibit cell infectivity of the virus.

8 Claims, 6 Drawing Sheets

METHOD OF TREATING HERPES SIMPLEX VIRUS INFECTION

1. FIELD OF THE INVENTION

The present invention relates to a method for treating herpes simplex virus (HSV) infections.

2. REFERENCES

Erlich, K. S., et al., N. Eng. J. Med. 320:293-296 (1989).
Hansch, C., Leo, A., Structure-Activity Correlation, Wiley, (1979).
Mertz, G. J., et al., JAMA 260:201-206 (1988).
Poh, Bo-Long, et al., Tetrahedron Letters, 30(8):1005 (1989).
Poh, Bo-Long, et al., Tetrahedron, 46(10):3651 (1990).
Poh, Bo-Long, et al., Tetrahedron, 46(12):4379 (1990).
Roizman, B., et al, Inter. Virol. 16:201-217 (1981).
Spear, P. G. [Roizman, B., Editor], The Herpes Simplex Viruses, Vol. 3, Plenum Press, N.Y., pp. 315-356 (1989).

3. BACKGROUND OF THE INVENTION

Herpes simplex virus-1 (HSV-1) and herpes simplex virus-2 (HSV-2) are present as either lytic or latent herpes viruses, and are the causative agents in cold sores (HSV-1) and genital herpes, typically associated with lesions in the region of the eyes, mouth, and genitals (HSV-2) (Roizman, Spear). Both HSV-1 and HSV-2 viral infections are recurrent infections, often existing in a repressed condition which can be activated in the form of lesions by a variety of stimuli.

Herpes infection can be treated with acyclovir, an acyclic nucleoside. The drug usually works in primary viral infection to limit the severity of infection. However, viral infection often recurs after drug treatment is stopped, and resistance to the drug may limit its usefulness over an extended treatment period (Erlich, Mertz).

4. SUMMARY OF THE INVENTION

One general object of the invention is to provide a method for inhibiting cell infection by HSV-1 and HSV-2.

The invention includes a method of inhibiting cell infection by HSV-1 or HSV-2 by contacting the virus with a macrocyclic compound composed of subunits of a chromotropic acid derivative linked between the 2 and 7 ring positions of adjacent subunits by methylene-linked bridges.

In one general embodiment of the method, the compound has the form:

where $R_1$ is a polar, hydrogen accepting substituent, preferably OH or an uncharged, carbon-containing substituent containing am oxygen atom linked directly to the naphthalene ring, or a sulfonyl or sulfonamide group, $R_2$ is sulfonic acid, a sulfonate salt, or a sulfonamide, $R_3$ is H or an uncharged or negatively charged substituent with a log(octanol/water partition coefficient) value less than 1, and $R_4$ is a 1 to 3 atom-chain bridge linking each naphthalene group through a naphthalene-ring carbon-methylene linkage.

In a related aspect, the invention provides a method of inhibiting cell infection by HSV-1 or HSV-2 by contacting the virus with a macrocyclic compound (a) composed of subunits of a chromotropic acid derivative linked between the 2 and 7 ring positions of adjacent subunits by methylene-linked bridges, and (b) effective to inhibit binding of HSV-1 or HSV-2 to virus-infectable cells.

In another related aspect, the invention provides a method of inhibiting cell infection HSV-1 or HSV-2 by contacting the virus with a macrocyclic naphthalene compound effective to bind selectively to HSV-1 or HSV-2 envelop proteins, as evidenced by protein-specific binding of the compounds to HSV-1 or HSV-2 envelop proteins fractionated by sodium dodecyl sulfate polyacrylamide gel electrophoresis.

The compound may be contacted with the virus by topical administration of the compound to a region of infection, by oral or parenteral administration, by application to a mucosal membrane, such as by intranasal administration, or by inhalation.

These and other objects and features of the invention will become more fully apparent when the following detailed description of the invention is read in conjunction with the accompanying drawings.

DETAILED DESCRIPTION OF THE INVENTION

I. Synthesis of Macrocyclic Chromotropic Acid Compounds

Figure 1A:
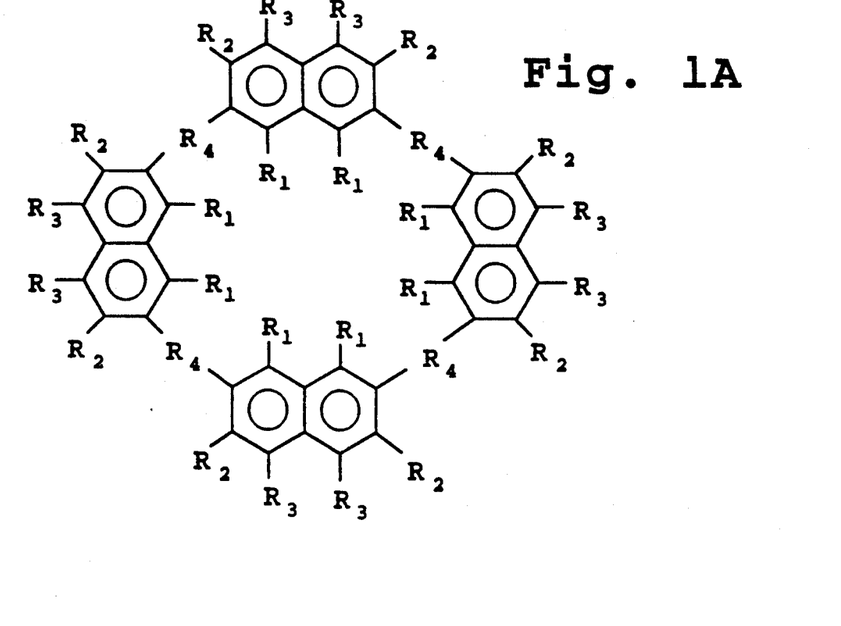
FIG. 1A and 1B shows the structural formula of a tetrameric macrocyclic chromotropic acid compound (A) and its structural equivalent (B) used in the invention.
Figure 1B:
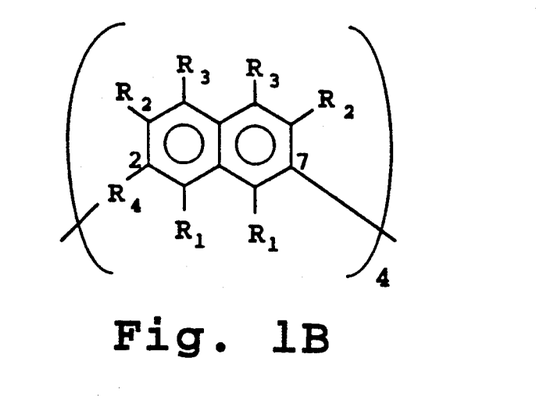

This section describes the synthesis of chromotropic acid macrocyclic compounds useful in practicing the present invention. As defined herein, "chromotropic acid macrocyclic compound" means a macrocyclic compound composed of subunits of a chromotropic acid derivative, where each subunit is linked between its 2 ring position and the 7 ring position of an adjacent subunit by a methylene-linked bridge. FIG. 1 shows the general structural formula of a tetrameric chromotropic acid macrocyclic compound, with the 2 and 7 positions of each subunit indicated. The subunits of a chromotropic acid derivative in the compound are represented by the structures:

where $R_4$ represents the methylene linked bridge. As will be seen below, preferred macrocyclic chromotropic acid compounds for use in the invention preferably include the chromotropic acid derivatives in which $R_1$ is a polar, hydrogen accepting substituent, preferably OH or an uncharged, carbon-containing substituent containing an oxygen atom linked directly to the naphthalene ring; $R_2$ is sulfonic acid, a sulfonate salt, or a sulfonamide; and $R_3$ is H or an uncharged or negatively charged substituent with a log(octanol/water partition coefficient) value less than 1.

Also as will be seen below, the $R_4$ bridge linking the chromotropic acid derivative subunits is preferably of the form $>$CHR where R is H or a small carbon-containing group, such as lower alkyl, alkenyl, ketone, or carboxylic acid group, or aryl group, or of the form —$CH_2NR'CH_2$—, where R' is similarly H or a small carbon containing group, such as a lower alkyl group. In the embodiment in which $R_4$ has the form $>$CHR, bridged naphthalene groups are linked by a single methylene ($>CH_2$) group. In the embodiment in which $R_4$ has the form —$CH_2NR'CH_2$—, bridged naphthalene groups are linked by the two methylene groups at opposite ends of the bridge. More generally, the chromotropic acid subunits are linked by a single methylene group forming the bridge, or by methylene groups at opposite ends of the bridge.

Representative macrocyclic compounds which have been synthesized and tested for anti-viral activity are identified by their $R_1$, $R_2$, $R_3$, and $R_4$ substituents in Table 1 below. The KY number in the left-hand column in the Table refers to the analog designation of the corresponding compound. For example, the compound in which $R_1$ is OH, $R_2$ is $SO_2NH_2$, $R_3$ is H, and $R_4$ is —$CH_2$— is designated KY-3.

TABLE 1

| KY  | $R_1$ | $R_2$ | $R_3$ | $R_4$ |
|-----|-------|-------|-------|-------|
| 1   | OH    | $SO_3Na$ | H | —$CH_2$— |
| 3   | OH    | $SO_2NH_2$ | H | —$CH_2$— |
| 42  | OH    | $SO_3Na$ | H | $>$CHCO$_2$H |
| 48  | OH    | $SO_3Na$ | H | $>$CHCHOHCH$_2$OH |
| 85  | OH    | $SO_3Na$ | OH | $>$CHC$_6$H$_6$ |
| 97  | OH    | $SO_3Na$ | H | $>$CH$_2$CH=CH$_2$ |
| 110 | OH    | $SO_3Na$ | H | $>$CHC(O)CH$_3$ |
| 121 | OH    | $SO_2C_6H_3(OH)_2$ | H | —$CH_2$— |
| 123 | OH    | $SO_2Na$ | H | —$CH_2$— |
| 143 | OH    | $SO_3Na$ | OH | —$CH_2$— |
| 147 | OH    | $SO_2NHCH_3$ | H | —$CH_2$— |
| 148 | OH    | $SO_2NHEt$ | H | —$CH_2$— |
| 151 | $OCH_3$ | $SO_3Na$ | H | —$CH_2$— |
| 158 | OH    | $SO_2CH_3$ | H | —$CH_2$— |
| 175 | OH    | $SO_3CH_3$ | H | —$CH_2$— |
| 176 | OH    | $SO_2NHC_6H_6$ | H | —$CH_2$— |
| 193 | OH    | $SO_3Na$ | Br | $>$CHBrCH$_2$Br |
| 194 | OH    | $SO_3Na$ | Br | —$CH_2$— |
| 270 | $OCOCH_3$ | $SO_3Na$ | H | —$CH_2$— |

TABLE 1-continued

| KY | $R_1$ | $R_2$ | $R_3$ | $R_4$ |
|---|---|---|---|---|
| 272 | OCOCH$_3$ | SO$_3$Na | H | >CHCO$_2$H |
| 276 | OCOEt | SO$_3$Na | H | —CH$_2$— |
| 277 | OCOEtCl | SO$_3$Na | H | —CH$_2$— |
| 280 | OCH$_3$ | SO$_3$Na | H | —CH$_2$— |
| 281 | OCOC$_3$H$_7$ | SO$_3$Na | H | —CH$_2$— |
| 284 | OCH$_3$ | SO$_3$Na | H | >CHCO$_2$H |
| 289 | OCOC$_4$H$_9$ | SO$_3$NH$_4$ | H | —CH$_2$— |
| 291 | OCOC$_5$H$_{11}$ | SO$_3$NH$_4$ | H | —CH$_2$— |
| 293 | OCOCH=CHCH$_3$ | SO$_3$NH$_4$ | H | —CH$_2$— |
| 294 | OCO(CH$_2$)$_6$CO$_2$H | SO$_3$NH$_4$ | H | —CH$_2$— |
| 307 | OCO(CH$_2$)$_5$CO$_2$H | SO$_3$NH$_4$ | H | —CH$_2$— |
| 313 | OH | SO$_3$Ca$^{\frac{1}{2}}$ | H | —CH$_2$— |
| 314 | OH | SO$_3$Ba$^{\frac{1}{2}}$ | H | —CH$_2$— |
| 346 | OH | SO$_3$Na | H | —CH$_2$N(CH$_3$)CH$_2$— |
| 376 | OH | SO$_3$NHCH$_2$CO$_2$H | H | —CH$_2$— |
| 395 | OCH$_3$ | SO$_3$Na | H | —CH$_2$N(CH$_3$)CH$_2$— |
| 397 | OCH$_3$ | SO$_2$NH2 | H | —CH$_2$— |
| 398 | OCH$_3$ | SO$_2$NHCH$_2$CO$_2$H | H | —CH$_2$— |
| 399 | OCH$_3$ | SO$_3$NHCH$_2$CO$_2$H | H | —CH$_2$N(CH$_3$)CH$_2$— |

Figure 2A:
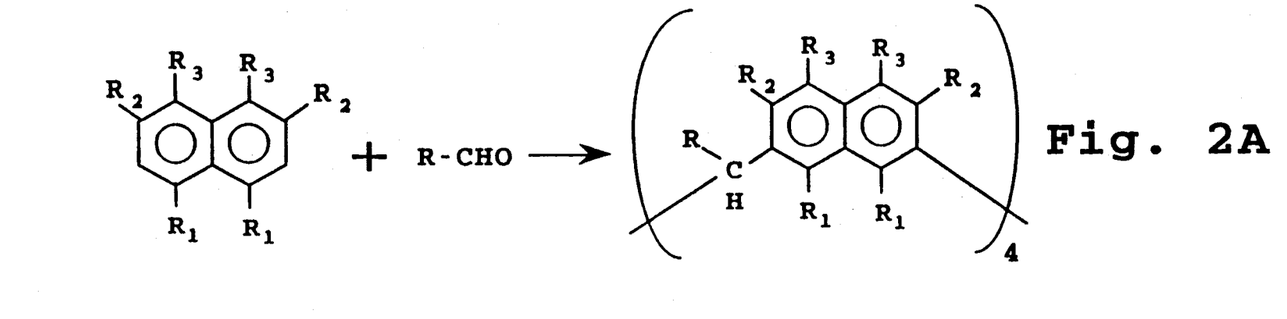
FIGS. 2A and 2B illustrate two general methods of synthesis of a tetrameric chromotropic acid compound.
Figure 2B:
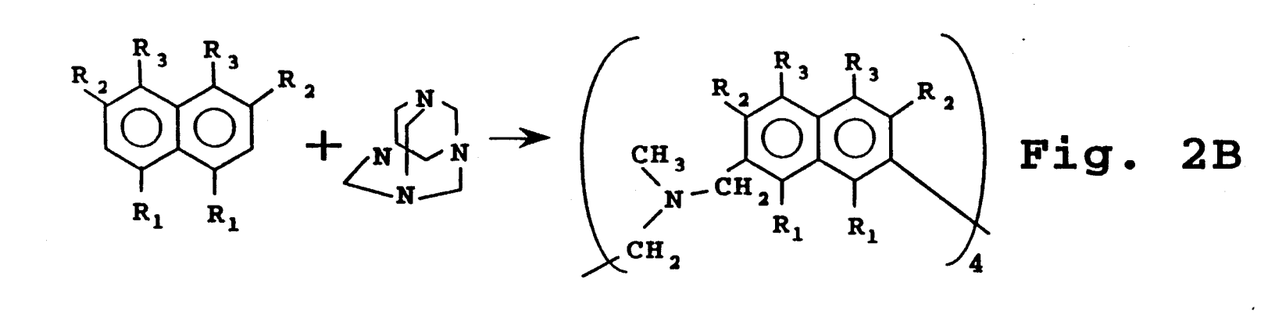

FIGS. 2A and 2B illustrate two preferred synthetic methods for preparing macrocyclic chromotropic acid compounds. The method illustrated in FIG. 2A involves cyclization of a chromotropic acid derivative (which is defined herein to include chromotropic acid itself) with an aldehyde (R—CHO) to form a macrocyclic compound, such as the tetramer shown FIG. 1, in which the chromotropic acid subunits are linked by R-substituted methylene groups, i.e., in which $R_4$ is >CHR. This synthetic scheme provides a convenient method for constructing macrocyclic compounds having a variety of different bridge-methylene R groups, by carrying out the cyclization reaction in the presence of an aldehyde of the form R—CHO.

For example, to construct a macrocyclic compound with a —CH$_2$— bridge, such as the KY-1 compound, the chromotropic acid derivative is reacted with formaldehyde. Typical reaction conditions are given in Example 1A for the synthesis of KY-1. Similarly, KY-42 is prepared by cyclization with glyoxylic acid (Example 1C); KY-48, in the presence of glyceraldehyde; KY-85, in the presence of benzaldehyde; KY-97, in the presence of acrolein; and KY-110, in the presence of pyruvic aldehyde. It will be appreciated that a variety of other RCHO aldehydes having small alkyl, alkenyl, acid and other hydrocarbon R groups would be suitable. Further the R bridge group may be further modified after the cyclization reaction. For example, KY-193 may be prepared by bromination of the KY-97 compound.

In the method illustrated in FIG. 2B, cyclization of the chromotropic acid derivatives is carried out by reaction with hexamethylenetetramine, to form a 3-atom chain bridge of the type —CH$_2$N(CH$_3$)CH$_2$—. The cyclization reaction for the synthesis of KY-346 is given in Example 1K. The —CH$_2$N(CH$_3$)CH$_2$— bridge may be modified, after the cyclization reaction, to form a variety of N-substituted bridges of the —CH$_2$N(R')CH$_2$—, where R' is one of a variety of small carbon-containing groups, according to known synthetic methods.

For synthesis of macrocyclic compounds with selected $R_1$, $R_2$, and $R_3$ substituents, two general approaches are available. In one approach, the chromotropic acid derivative is modified prior to cyclization so that the cyclized product will either contain the selected $R_1$, $R_2$, and $R_3$ substituent, or contain a substituent which can be readily modified to the selected substituent. This approach is illustrated by the synthesis of KY-147, which has an SO$_2$NHCH$_3$ $R_2$ substituent. Here the sodium salt of chromotropic acid ($R_2$=SO$_3$Na) was reacted first with sulfonylchloride, to form the corresponding $R_2$=SO$_2$Cl derivative, which was then further reacted with methylamine to form the desired $R_2$=SO$_2$NHCH$_3$ derivative. Cyclization of the derivatized subunit with formaldehyde produces KY-147. Details of the reaction are given in Example 1E. A similar strategy was employed for the synthesis of KY-148 ($R_2$=SO$_2$NHCH$_2$,CH$_3$) by final subunit reaction with ethylamine, and for the synthesis of KY-176 ($R_2$=SO$_2$NHC$_6$H$_6$) by final subunit reaction with benzyl amine.

By way of example, macrocyclic compounds with a variety of $R_1$ substituents may be prepared by modification of chromotropic acid prior to cyclization. In synthesizing KY-151 ($R_1$=OCH$_3$) chromotropic acid is reacted with dimethylsulfate under basic conditions, as detailed in Example 1F, to form the dimethylether of chromotropic acid. Cyclization of the derivatized subunit by reaction with formaldehyde leads to the desired macrocyclic product. Similarly, in preparing KY-307 ($R_1$=O(CH$_2$)$_5$CO$_2$H), chromotropic acid is first converted to the diether of hexanoic acid by initial reaction of chromotropic acid with 6-bromohexanoic acid under basic reaction conditions.

In a second general approach, the selected substituent is formed on the subunit naphthalene rings by derivatization of the naphthalene rings after cyclization to form a naphthalene-ring macrocyclic structure. For example, in preparing the compounds KY-270 through KY-294, in which $R_1$ has the form OCOR, the macrocyclic compound formed by cyclization of chromotropic acid is reacted with an acid chloride of the form RCOCl, under basic conditions, as detailed in Example 1K for the synthesis of KY-270.

This approach is further illustrated by the synthesis of KY-3 ($R_2$=SO$_2$NH$_2$). Here KY-1 was treated with chlorosulfonic acid, to form the corresponding $R_2=SO_2Cl$ compound, which was then converted to the $R_2=SO_2NH_2$ compound by reaction with ammonia. Details are given in Example 1B.

For the synthesis of KY-123 ($R_2=SO_2Na$), KY-1 is initially reacted with chlorosulfonic acid, and the resulting acid chloride derivative is reacted with sodium sulfite to reduce the sulfonate groups to sodium sulfonyl groups, as detailed in Example 1D. For the synthesis of KY-158 ($R_2=SO_2CH_3$), KY-1 is treated with sulfonylchloride, to form the corresponding sulfonylchloride derivative, then reacted with sodium sulfite in the presence of bicarbonate to form the sodium sulfonyl $R_2$ groups. Further reaction with sulfonyl chloride produces the corresponding sulfonyl chloride, and with $NaOCH_3$ produces the desired $R_2=SO_2CH_3$ substituents. Reaction details are given in Example 1H. For the synthesis of KY-175 ($R_2=SO_3CH_3$), KY-1 is reacted with sulfonylchloride, as above, to produce the corresponding $R_2=SO_2Cl$ substituents. Further reaction with $NaOCH_3$ leads to the desired $R_2$ substituent. Reaction details are given in Example 1I.

The syntheses of KY-193 and KY-193 represent another example a synthetic scheme involving derivatization of the naphthalene subunits after cyclization. Here the selected macrocyclic compound, in the case, KY-1 or KY-97, is brominated with $Br_2$ under conditions which selectively brominate the $R_3$ ring positions of the naphthalene subunits.

It will be appreciated that the synthetic method for forming selected-substituent macrocyclic compounds may include both prior derivatization of chromotropic acid and subsequent derivatization of the subunits after cyclization. For example, in forming KY-397 ($R_1=OCH_3$, $R_2=SO_2NH_2$), chromotropic acid subunits are first reacted at the $R_1$ positions, to form the dimethyl ether derivative as described above. After cyclization with formaldehyde, the compound is further derivatized at the $R_2$ position, also as described above, to convert the $SO_3$ group to the desired $SO_2NH_2$ substituent.

The KY compounds described above can be converted readily to a variety of sulfonic acid or sulfonate salts, by reaction in acid or in the presence of a suitable salt, according to well known methods. Thus, for example, several of the KY compounds shown in Table 1 are ammonium salts formed by cation exchange of sodium cation in the presence of an ammonium salt, such as ammonium chloride. In addition, exposure of the macrocyclic compound to a variety of metal cations, such as the cations of Ca, Ba, Bi, Ge, Zn, La, Nd, Ni, Hf, or Pb, may produce both a metal salt and a metal chelate of the macrocyclic compound in which the metal is chelated at interior polar pocket in the compound.

The physical properties of several macrocyclic compounds prepared in accordance with the invention have been studied by absorption and mass spectrometry and by nuclear resonance spectroscopy (NMR), as detailed in Examples 1A, 1B, 1C, and 1K. These compounds are tetrameric macrocyclic compounds, such as indicated in FIG. 1, or predominantly tetrameric and octameric compounds. Macrocyclic compounds formed by cyclization of as few as three and as many as eight chromotropic acid derivative subunits are also contemplated.

II. Inhibition of HSV Infectivity

Representative compounds from Table 1 were examined for toxicity in cell culture, using a panel of human cell lines, as detailed in Example 2. The drug was added to cell cultures at a final concentration of 5, 10, 25, 50, or 100 μg/ml. Three days later the cells were washed to remove drug, and stained with a vital stain, to detect dead (stained) cells.

The $IC_{50}$ drug concentration, defined as the concentration of drug which produces 50% cell death, was 50 μg/ml for KY-143, and 100 μg/ml or greater for all of the other compounds tested. For KY-1, which has a molecular weight of 1321 daltons, a drug concentration of 100 μg/ml is equivalent to about 76 μM.

Representative KY compounds from Table 1 were tested for inhibition of cytopathic effects in cultured, HSV-infected cells. In the method reported in Example 3, Vero cells were infected with HSV-1 or HSV-2 and allowed to grow in culture until cytopathic effects were clearly visible. In the absence of infection, the cells form an even monolayer of fibroblast-like cells. With HSV infection, a cytopathic effect characterized by round cells in suspension is clearly evident after 24 hours, followed by clumping and lysis after 2-3 days.

In the drug inhibition study reported in Example 3, cells were exposed to HSV-1 or HSV-2 virus and, at the same time, to a selected KY compound, at a final compound concentration of 10 μg/ml. Two hours later, the cells were washed to remove drug and virus, and 24 hours later the cells were examined for cytopathic effect. If a clear cytopathic effect was not observed with 10 μg/ml of the drug, the study was repeated at a drug concentration of 20 μg/ml. All of the compounds shown in Table 2 below were effective in inhibiting cytopathic effects at 10 or 20 μg/ml.

The compounds from Table 1 were further tested for activity against HSV infection in a plaque reduction assay, as detailed in Example 4. Here Vero cells, after overnight incubation, were exposed to serial dilutions of KY compound, from 0.625-10 μg/ml, and HSV-1 or HSV-2 virus for two hours. After washing to remove drug and extracellular virus, the cells were further incubated for 2 days, then stained and counted for plaque formation. Percent inhibition was determined by dividing plaques produced by total number of plaques in infected, untreated controls. From the dose response curve of plaque inhibition (expressed as percent of control), the dose required to produce 50% plaque reduction, $ED_{50}$, was determined. The $ED_{50}$ values for infection by HSV-1 and HSV-2 infection is given in the right-hand columns in Table 2.

TABLE 2

| KY | $ED_{50}$ (μg/ml) HSV-1 | HSV-2 |
|---|---|---|
| 1 | 2.7 | 1.7 |
| 3 | 2.5 | 1.8 |
| 121 | 1.5 | 1.8 |
| 123 | 1.5 | 2.5 |
| 151 | 1.2 | 1.8 |
| 194 | 1.0 | 1.0 |
| 270 | 2.0 | 2.0 |
| 276 | 1.3 | 1.2 |
| 277 | 1.0 | 1.2 |
| 280 | 1.1 | 1.0 |
| 281 | 0.5 | 1.5 |
| 284 | 1.0 | 1.6 |
| 289 | 2.2 | 1.7 |
| 291 | 1.4 | 2.0 |
| 293 | 1.9 | 2.7 |

TABLE 2-continued

| KY | $ED_{50}$ ($\mu$g/ml) HSV-1 | HSV-2 |
|---|---|---|
| 294 | 1.0 | 2.2 |
| 307 | 0.7 | 2 |
| 376 | 2.7 | 1 |

With reference to Tables 1 and 2, it is seen that compounds with highest anti-HSV activity (the compounds in Table 2, which inhibit CPE effects in Vero cells at a drug concentration of less than 10-20 μg/ml) have the following chemical-group substituents: $R_1$ is a polar substituent which is able to hydrogen bond. Exemplary substituents are OH, alkoxy groups, such as $OCH_3$, or an ester, such as $OCOCH_3$, and esters of larger organic groups. $R_2$ is a sulfonic acid, sulfonate salt, or sulfonamide. $R_3$ is H or a halide (e.g., Br). Both of these are reasonably hydrophilic substituents as evidenced by a log(octanol/water partition coefficient) value less than 1 (Hansch, Table VI-I). Studies conducted in support of the invention indicate that activity is relatively insensitive to the substituent at this position.

Compounds having a variety of $R_4$ groups of the form >CHR, where R is a lower alkyl, alkenyl, ketone, or carboxylic acid, as well $R_4$ groups of the form—$CH_2N(CH_3)CH_2$— are active in inhibiting HSV infectivity.

Figure 3A:
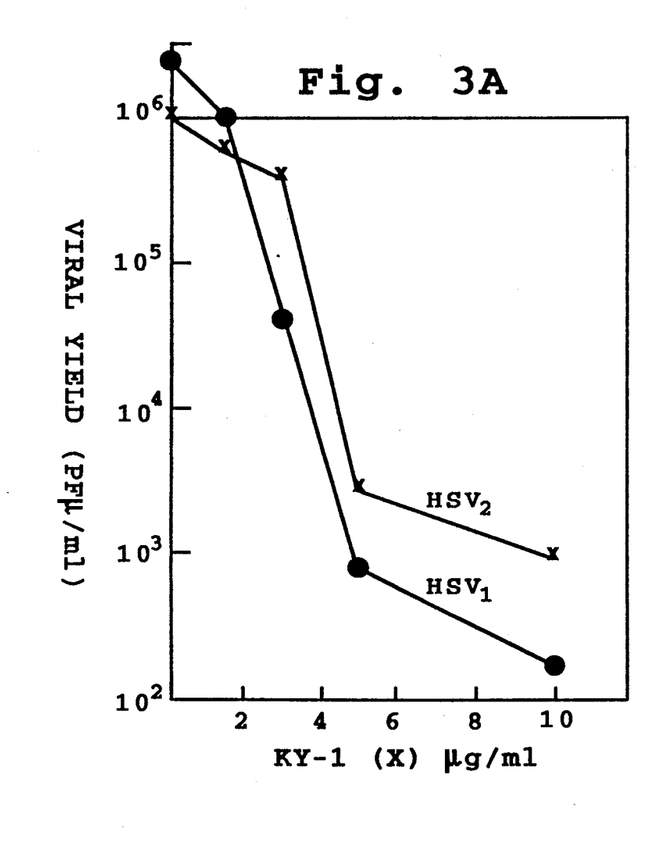
FIGS. 3A and 3B are plots of HSV viral yields, as a function of drug dose, for the compounds KY-1 (3A) and KY-42 (3B)
Figure 3B:
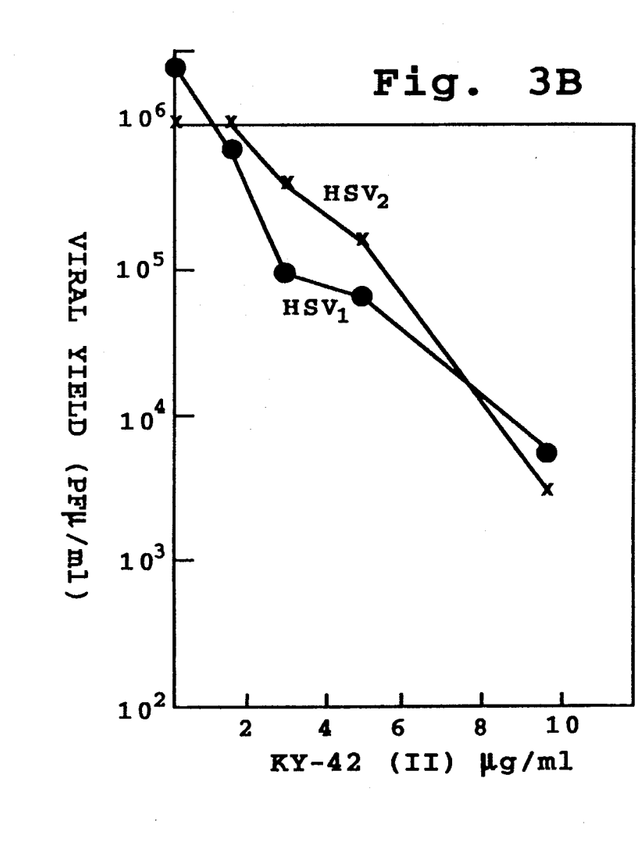

The ability of selected KY compounds to inhibit HSV-1 and HSV-2 viral yield at selected drug concentrations up to 10 μg/ml was assessed in the viral inhibition assay described in Example 5. Briefly, cultured Hela cells were exposed to serially diluted KY compound and virus, allowed to grow for 24 hours, then freeze/thawed 3 times to release virus particles. Vero cells were infected serial dilutions of the viral lysates were assayed for plaque counts as above. The drop in viral yield, as a function of drug concentration, is plotted in FIGS. 3A and 3B for compounds KY-1 and KY-42 respectively. The dose dependent drop in viral yield was between about 3-5 orders of magnitude, depending on drug and virus. The degree of inhibition of viral yield was generally greater for HSV-1 than for HSV-2. Similar results were observed with several other KY compounds.

The inhibitory effect of KY-1 against drug-resistant strains of HSV-1 and HSV-2 was compared with several anti-viral agents which have been used in treating HSV infection. These compounds tested were the nucleoside analogs acyclovir (ACV), ganciclovir (DHPG), phosphonoformate (PFA), and phosphomethoxyethyladenine (PMEA). Inhibition of viral yield was determined, as above, by infecting Hela cells in the presence of wild type or drug-resistant strains of HSV-1 or HSV-2, and serial dilutions of a selected anti-viral compound, and infecting Vero cells with serial dilutions of the Hela cell lysate, as above. Details of the inhibition study are given in Example 6.

The $ID_{90}$ concentration which effects 90% inhibition of viral yield is given in Table 3. The KOS (HSV-1) and 333 (HSV-2) are wild type viruses; the KOS(PMEA)' and KOS(PFA)' are drug-resistant HSV-1 strains having a DNA polymerase mutation. The 333(DHPG) strain is a drug-resistant HSV-2 strain having a thymidine kinase mutation. With the exception of DHPG as an inhibitor of drug-resistant strains of HSV-1, and PMEA as an inhibitor of drug-resistant strains of HSV-2, all of the nucleoside analogs were at least about 20 times less active against drug-resistant strains than wild-type strains of either HSV-1 or HSV-2, as measured by drug concentration required to inhibit yield. By contrast, the KY compound showed substantially the same specific activity against drug-resistant strains of HSV-1 and HSV-2 as against wildtype strains.

TABLE 3

| Virus | Strain/ drug selection | Mutation Locus | Drug tested ($ID_{90}$) # | | | | |
|---|---|---|---|---|---|---|---|
| | | | KY-1 ($\mu$g/ml) | ACV ($\mu$M) | DHPG ($\mu$M) | PFA ($\mu$M) | PMEA ($\mu$M) |
| HSV-1 | KOS | None | 1.9 | 14 | 2 | 180 | 100 |
| | KOS(PMEA)' | DNA pol | 2.6 | 380 | NT | 3000 | >2000 |
| | KOS(PFA)' | DNA pol | 4.3 | 100 | 1 | >1000 | >1000 |
| HSV-2 | 333 | None | 3.2 | ≈10 | 2 | 150 | 155 |
| | 333(DHPG)' | TK | 3.7 | >100 | 215 | NT | 120 |

The data demonstrate that KY-1 is effective against drug-resistant HSV strains at drug concentrations comparable to those which are effective against wild type virus strains. By contrast, and with the exception of DHPG as an inhibitor of HSV-1 strains, both drug-resistant strains showed a significant resistance to ACV, DHPG, PFA, and PMEA, as evidenced by the several-fold greater $ID_{90}$ drug concentrations required for virus inhibition.

III. Compound Binding to HSV

The studies reported in this section show that the compounds of the invention bind selectively to HSV proteins, including virus envelop glycoproteins. This binding is effective to inhibit viral attachment to infectable cells, and explains, at least in part, the mechanism by which macrocyclic chromotropic acid compounds are able to inhibit cell infectivity by HSV.

Figure 4:
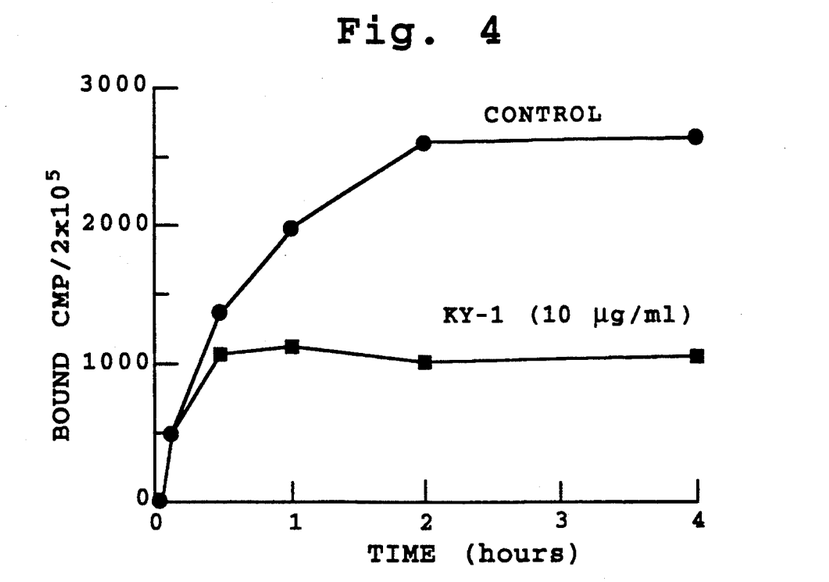
FIG. 4 shows the inhibition of $^3$H-labeled HSV-1 binding to cells by the compound KY-1.

In the binding study reported in Example 7, Vero cells were exposed to radiolabeled HSV-1 or HSV-2 virus, either in the presence of absence of KY-1, and the binding of virus to the cells at times up to 4 hours after exposure to the virus was measured. FIG. 4 shows a plot of virus (radiolabel) binding to cells over the four-hour incubation period. In the absence of drug, the amount of bound virus increased steadily over two hours, and slightly from 2-4 hours. By contrast, virus binding to cells peaked at about ½ hour in the presence of drug, presumably reflecting the time during which the binding events effective to block virus binding to the cells are equilibrating.

The ability of KY compounds to block HSV attachment to infectable cells could be explained by drug binding to virus receptor sites on the cell surface, or alternatively, by drug binding to virus recognition sites, in either case, serving to block virus attachment to otherwise-infectable cells. The drug-to-cell binding mechanism would predict that cells might be successfully protected from HSV infection by pretreating the cells with a KY compound, and removing the drug prior to cell exposure to virus. The drug-to-virus binding mechanism would require pre-exposing the virus to drug before cell infection.

This question was examined in the study reported in Example 8. In one group, Vero cells were first exposed to serial dilutions of KY-1, at the concentrations indicated in FIG. 5. Two hours later, the cells were washed to remove free drug, then exposed to HSV virus. The reduction in plaque formation, expressed as a percent of control, is shown closed rectangles in FIG. 5. Little or no inhibition of HSV infection was achieved. Similarly, when cells were first exposed to virus for two hours, then exposed to drug, only a slight reduction in plaque formation was observed (open rectangles). By contrast, the inhibition in plaque formation was highly dose-dependent and nearly complete at 10 μg/ml drug concentration when cells were exposed at the same time to both drug and virus (solid circles). The results, combined with those shown in FIG. 4, indicate that KY compound inhibition of HSV (HSV-1 or HSV-2) involves drug binding to the virus, and consequent inhibition of virus attachment to cells.

This mechanism was examined further by studies on HSV-1 virus preincubated with KY compounds. In this study, which is detailed in Example 9, purified HSV-1 virus suspensions were incubated in the presence of KY-1, KY-217, or a control solution for 1 hour, then serially diluted to drug concentrations between $10^1$ to $10^{-4}$ μg/ml. Addition of the serially diluted virus suspensions gave the plaque counts, measured in duplicate, shown in Table 4. The "X" symbol in the table indicates plaques too numerous to count.

The results of the study demonstrate that inhibition of HSV infection by KY compounds is due, at least in part, to binding of drug to HSV particles. Complete virus inhibition was seen at drug final drug concentration of $10^{-2}$ to $10^{-4}$ μg/ml (which are much lower than those needed to inhibit HSV in Vero cell culture), From this, it can be concluded that the drug-binding/inaction of the virus is effectively irreversible, i.e., not reversed by high dilution effects.

TABLE 4

| KY Compounds | Initial Viral Input (pfu/cell) | Plague number after serial 10-time dilutions | | | | | |
|---|---|---|---|---|---|---|---|
| | | 1 | $10^1$ | $10^2$ | $10^3$ | $10^4$ | $10^5$ |
| Control | 0.3 | XX | XX | XX | 50,41 | 9,4 | 0,0 |
| (media only) | 3 | XX | XX | XX | XX | 38,49 | 8,4 |
| KY 1 | 0.3 | 3,2 | 0,0 | 0.0 | 0,0 | 0,0 | 0,0 |
| (10 μg/ml) | 3 | 2,2 | 2,1 | 17,16 | 5,2 | 0,0 | 0,0 |
| KY 217 | 0.3 | 2,8 | 3,3 | 0,0 | 0,0 | 0,0 | 0,0 |
| (10 μg/ml) | 3 | XX | XX | 6,0 | 5,5 | 0,0 | 0,0 |

Figure 6:
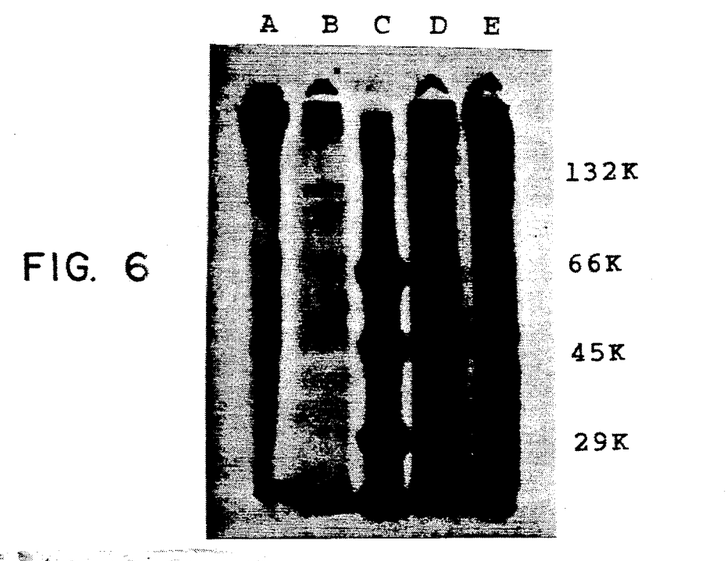
FIG. 6 shows SDS-PAGE autoradiograms of HSV-1 proteins in the presence (lane A) and absence (lane B) of mercaptoethanol, and of HSV-2 proteins in the presence (lane C) and absence (lane D) of mercaptoethanol, all with bound radiolabeled KY-1, and stained marker proteins (lane E)
Figure 7:
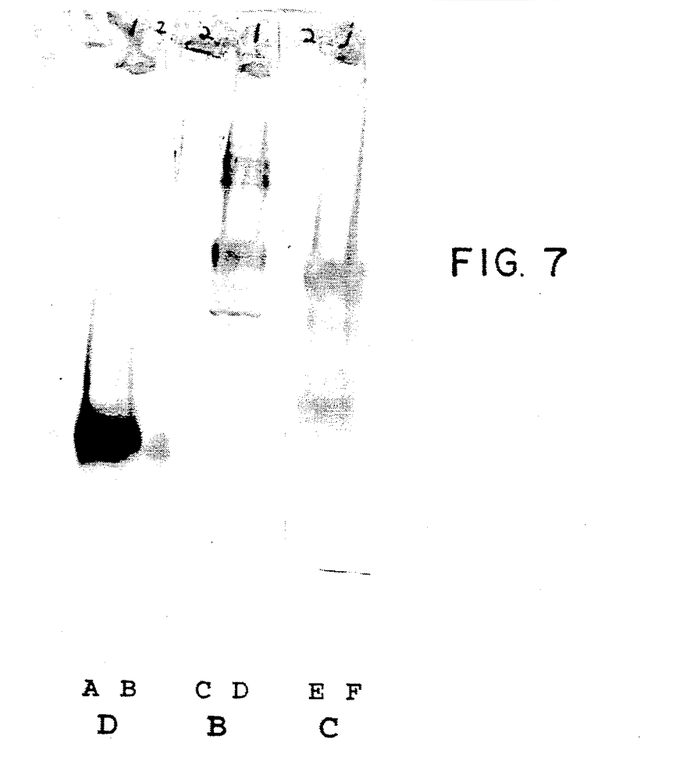
FIG. 7 shows SDS-PAGE autoradiograms of radiolabeled KY-1 compound bound to HSV-1 glycoproteins gD (lanes A and B), gB (lanes C and D), and gC (lanes E and F)

When radiolabeled KY-1 compound is bound to HSV-1 or HSV-2 virus, and the virus proteins then fractionated by sodium dodecyl sulfate polyacrylamide gel electrophoresis (SDS-PAGE), the binding patterns seen in FIG. 6 are observed. Lanes A and B in the figure are autoradiographs of HSV-1 proteins in the presence (lane B) and absence (lane B) of mercaptoethanol, and lanes C and D, analogous patterns for HSV-2 proteins. The lane at the right contains the molecular weight markers, as indicated. The major bands of drug binding in HSV-1 have molecular weights, as determined from SDS-PAGE, of 45, 66, and about 130 kilodaltons. The major bands of drug binding in HSV-2 have similar molecular weights. The major bands which show KY binding in FIG. 6 were identified as HSV glycoproteins gD, gB, and gC, as shown in FIG. 7 and described in Example 10.

IV. Method of Inhibiting HSV Infectivity

In the method of the invention, a macrocyclic chromotropic compound effective to bind selectively to HSV-1 or HSV-2, or alteratively, to inhibit HSV-1 or HSV-2 binding to HSV-infectable cells is contacted with HSV-1 or HSV-2 virus, to inhibit viral infectivity. The method is useful in the treatment of HSV infection in a mammalian subject, by virtue of the ability to block initial infection of host cells by HSV-1 or HSV-2, and to block the spread of viral infection which occurs by viral lysis of infected cells and release of new virus.

The macrocyclic chromotropic compound used in the method may be administered topically, for example, by direct application to skin lesions. Alternatively, the compound may be administered orally or parenterally, for delivery of the compound to the bloodstream. In another embodiment, the compound is administered intranasally, or by direct application to mucosal tissue, or by inhalation for uptake by the lungs.

The dosage which is administered is a pharmaceutically effective dose, defined as a dose effective to inhibit viral infection of host cells. As seen above, compound doses in the range 1–10 μg/ml are generally effective in inhibiting viral infection of cells. Thus, for many applications, an effective dose would be one which produces a concentration of compound in this range at the site of infection. For topical administration, compositions containing between 1–5% KY compounds are suitable.

One requirement for effective treatment by parenteral administration is that the drug be available in the bloodstream in a form capable of binding to and inactivating HSV virus. A second requirement is that the drug halflife in the bloodstream be such as to provide inhibitory activity for preferably at least 4–8 hours after IV drug administration. In studies conducted in support of the present invention, in which male and female rats are given intravenous (IV) administration of KY-1, about 25% and 18% of the initial drug dose was present in the bloodstream of the female and male animals, respectively, four hours after compound administration. Other studies showed that the drug was present in the serum predominantly in free (non-complexed) form.

The availability of macrocyclic chromotropic acid compound with HSV-inhibitory activity after IV administration was also examined by injecting a KY compound, and for comparison, acyclovir, IV into an animal, and assaying the anti-HSV activity of serum from blood samples withdrawn from the animal at intervals 1 minute, 1 hour, and 2 hours after IV injection. The IV dose was a maximum tolerated dose (MTD) of KY-346 (about 75 mg/kg body weight) and acyclovir (about 100 mg/kg body weight). At these dosages, acyclovir would be expected to have an approximately eightfold greater molar concentration than that of the KY compound.

A serum fraction from the blood samples was added to Vero cells along with HSV-1 or HSV-2 at a virus concentration of either 0.3 and 3 PFU virus/cell, substantially as described in Example 3, and the cells were examined for cytopathic effect 1 day later. Table 5 below show the results of the study. Virus inhibition (no cytopathic effect) is indicated by a "+" symbol, and "N.P." in the table indicates normal plasma (control). The results show that both KY compound and acyclovir retain activity after exposure to serum for extended periods in the bloodstream.

TABLE 5

| Dilutions | Viral Inoculation | HSV-2/CPE KY-1 | | | | HSV-2/CPE KY-43 | | | |
|---|---|---|---|---|---|---|---|---|---|
| | | N.P. | 1 m | 1 h | 2 h | N.P. | 1 m | 1 h | 2 h |
| 1:100 | 3 | − | − | − | − | − | − | − | − |
| 1:50 | 3 | − | − | − | − | − | + | − | − |
| 1:25 | 3 | − | − | − | − | − | + | − | ± |
| 1:12.5 | 3 | − | ± | ± | ± | − | + | − | + |
| | | N.P. | | ACV | | N.P. | | ACV | |
| 1:100 | 3 | − | ± | − | − | − | ± | ± | − |
| 1:50 | 3 | − | ± | − | − | − | + | + | + |
| 1:25 | 3 | − | + | + | + | − | + | + | + |
| 1:12.5 | 3 | − | + | ± | + | − | + | + | + |

Thus it has been shown that KY compounds, when administered IV for treatment of systemic HSV infection, (a) are cleared relatively slowly from the bloodstream, (b) are present predominantly in free form, and (c) retain activity in inhibiting HSV infection.

In another embodiment of the invention, the drug is administered orally. Studies conducted in support of the application have shown that the drug, when administered orally, reaches the bloodstream in effective antiviral quantities. With reference to Table 6 below, animals were administered orally at 750 mg/kg (#1 and #2 animals), 1.5 g/kg (#3 and #4), and 2.25 g/kg (#5 and #6). Two and half hours after oral administration, plasma was obtained from the animals and diluted 12.5x, 25x, 50x, and 100x, and these dilutions were tested for ability to inhibit cytopathic effects in Vero cells infected with HSV-1 or HSV-2. The results are shown in Table 6. NP means "normal plasma". The righthand column in the table is the inhibition seen with KY-1 added to infected cells at the concentrations indicated. As seen, each oral dose produced effective anti-viral levels of drug in the bloodstream, with progressively higher levels being observed for the higher oral doses.

the compound at the vaginal orifice of an animal. Details of the method are given in Example 11. From FIG. 8A, which shows the level of drug in serum, it is seen that some drug passes into the bloodstream across the mucosal membrane, but is limited to very low drug levels—less than 1 µg/ml serum. The drug level at the topical site of administration, shown in FIG. 8B, indicates relatively high levels of drug at the site—greater than about 50 µg/swab—over the first four hours after drug administration.

To demonstrate the ability of the effectiveness of the method in reducing genital HSV-2 infection, animals were infected intravaginally with HSV-2, then treated topically three times daily beginning 6 hours or 48 hours after inoculation with HSV-2, as detailed in Example 15. Drug treatment was either saline control, KY-1, or acyclovir. Swabs of vaginal secretion were obtained and assayed for viral activity by a standard CPE assay. The severity of genital lesions was scored on a 0-5+ scale through a 21 day period of primary infection.

After HSV-2 inoculation, viral replication in the vaginal tract reached a peak on days 3-5, then declined gradually with most animals having cleared the virus by day 10. The effect of topical administration of the KY preparations on vaginal virus titers is summarized in Table 7. The animals treated with placebo at +6h or +48h had virus titer-day areas under the curve (AUC) values that were similar to the untreated control group. Viral replication in animals that received 5% or 1% KY-1 initiated 6h post-inoculation was decreased significantly when compared to the placebo-treated group (P <0.01 and P <0.05, respectively). The mean peak virus titers in treated animals were also decreased significantly compared with placebo-treated ones (5% KY-1 P <0.001 and 1% KY <0.01). Treatment with 5% ACV also reduced AUC values and mean peak vaginal virus titers when initiated at +6h but not at +48 h.

TABLE 6

| a Plasma Dilution (2.5 hr) | CPE (HSV₁) | | | | | | | b KY-1 µg/ml |
|---|---|---|---|---|---|---|---|---|
| | #1 | #2 | #3 | #4 | #5 | #6 | NP | |
| 100x | (−)− | (−)− | (+)− | (+)+ | (+)+ | (+)+ | (−)− | 2.5(+)± |
| 50x | (−)− | (−)− | (+)+ | (+)+ | (+)+ | (+)+ | (−)− | 5.0(+)+ |
| 25x | (±)− | (±)− | (+)+ | (+)+ | (+)+ | (+)+ | (−)− | 10 (+)+ |
| 12.5x | (+)± | (+)± | (+)+ | (+)+ | (+)+ | (+)+ | (−)− | 20 (+)+ |

| a Plasma Dilution (2.5 hr) | CPE (HSV₂) | | | | | | | b KY-1 µg/ml |
|---|---|---|---|---|---|---|---|---|
| | #1 | #2 | #3 | #4 | #5 | #6 | NP | |
| 100x | (−)− | (−)− | (±)− | (±)+ | (+)+ | (+)+ | (−)− | 2.5(+)− |
| 50x | (−)− | (−)− | (+)+ | (+)+ | (+)+ | (+)+ | (−)− | 5.0(+)− |
| 25x | (−)− | (−)− | (+)+ | (+)+ | (+)+ | (+)+ | (−)− | 10 (+)± |
| 12.5x | (±)± | (±)± | (+)+ | (+)+ | (+)+ | (+)+ | (−)− | 20 (+)+ | a = plasma were collected 2.5 hr. after oral administration of KY-1
b = KY- was done at 2% FCS
NP = Normal Plasma
+ = protection of CPE (3 PFu/cell)

In another embodiment of the method of the invention, for treating an HSV lesion on an exposed region of a subject, an inhibitory KY compound is contacted with HSV virus by applying the compound to the exposed region of the subject.

Figure 8A:
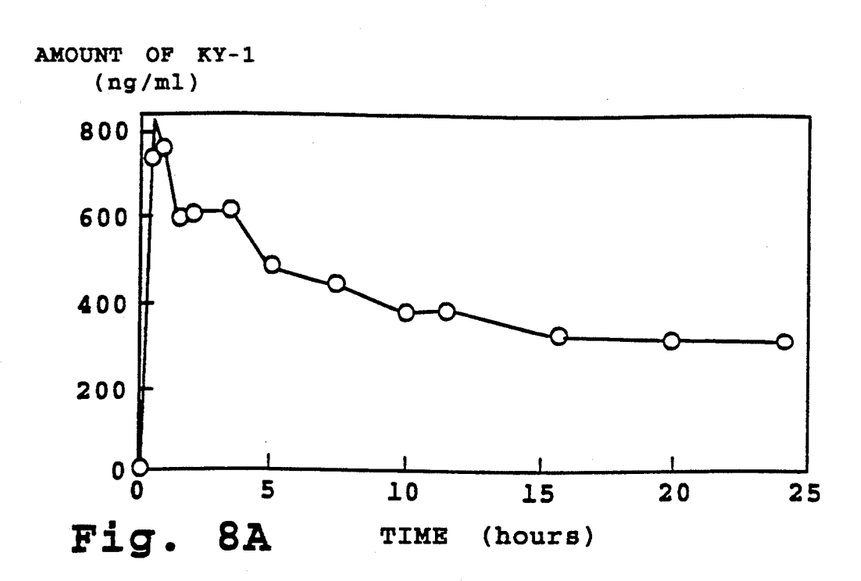
FIGS. 8A and 8B show the drug plasma concentration of KY-1 compound in rabbit over a 1-day period following IV administration (8A), and the drug concentration measured at a rabbit's vaginal orifice over a 1-day period following IV administration of the drug (8B).
Figure 8B:
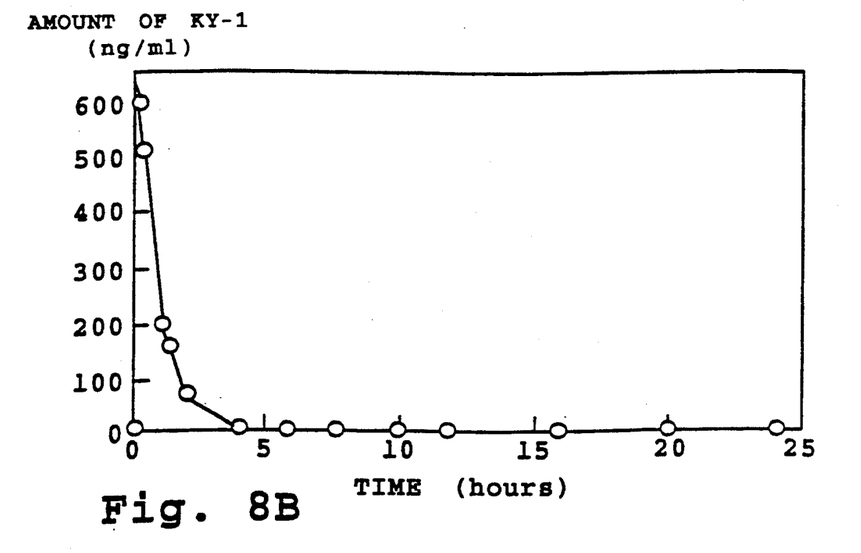

FIGS. 8A and 8B show the pharmacokinetics of a KY compound 24 hours after topical administration of

TABLE 7

| Treatment | Virus Score Day Area Under Curve | P-Value | Mean Peak Lesion Score | P-Value |
|---|---|---|---|---|
| Control | 23.0 | — | 4.2 | — |
| Placebo + 6 h | 23.2 | NS | 4.1 | NS |
| Placebo + 48 h | 21.0 | NS | 4.0 | NS |
| KY 5% + 6 hr | 10.9 | <0.01 | 2.4 | <0.001 |

TABLE 7-continued

| Treatment | Virus Score Day Area Under Curve | P-Value | Mean Peak Lesion Score | P-Value |
|---|---|---|---|---|
| KY 5% + 48 h | 19.7 | NS | 4.0 | NS |
| KY 1% + 6 h | 13.8 | <0.05 | 2.9 | <0.01 |
| KY 1% + 48 h | 20.4 | NS | 4.1 | NS |
| ACV 5% + 6 h | 9.0 | <0.01 | 2.4 | <0.001 |
| ACV 5% + 48 h | 14.5 | NS | 4.1 | NS |

Three to four days after HSV-2 inoculation, vesicular lesions appeared on the external genital skin. Lesions progressed to an ulcerative stage by days 7-8 and gradually healed by days 15-21. The effect of topical treatment with the KY preparations on lesion development and severity is shown in Table 8. The group treated with placebo at +6h had a significantly increased lesion score-day AUC (P <0.05); however, mean peak lesion scores were not different when compared to the untreated control group. Lesion development as determined by both AUC values and mean peak lesion scores was significantly reduced by treatment with 5% KY when given at 6h after infection compared to the placebo (P <0.001). Treatment with 1% KY significantly reduced the AUC at +6h (P <0.01) but not mean peak lesion scores.

TABLE 8

| Treatment | Lesion Score Day Area Under Curve | P-Value | Mean Peak Lesion Score | P-Value |
|---|---|---|---|---|
| Control | 37.0 | — | 3.6 | — |
| Placebo + 6 h | 47.0 | <0.05 | 3.9 | NS |
| Placebo + 48 h | 42.8 | NS | 3.6 | NS |
| KY 5% + 6 hr | 3.8 | <0.001 | 0.8 | <0.001 |
| KY 5% + 48 h | 45.7 | NS | 3.7 | NS |
| KY 1% + 6 h | 30.8 | <0.01 | 2.9 | NS |
| KY 1% + 48 h | 46.6 | NS | 4.3 | NS |
| ACV 5% + 6 h | 2.7 | <0.001 | 0.6 | <0.001 |
| ACV 5% + 48 h | 45.8 | NS | 3.8 | NS |

No sign of any skin irritation from any of the formulations was observed. Throughout the treatment period, the genital skin remained normal in appearance; no redness or swelling was observed. The guinea pigs also remained normal and healthy in appearance throughout the entire study.

The following examples illustrate methods for preparing and using macrocyclic naphthalene compounds in accordance with the invention. The examples are intended to illustrate, but not, the invention.

MATERIALS

All chemical reagents were obtained from Aldrich Chemical Co., or from other commercial sources.

EXAMPLE 1

Preparation of Anti-Viral Compounds

A. KY-1 ($R_1$=OH, $R_2$=$SO_3Na$, $R_3$=H, $R_4$=—$CH_2$—)

To a 41 mM aqueous solution (50 ml) of disodium chromotropic acid, 15 ml of 37% formaldehyde was added, giving a final molar ratio of 5:1 formaldehyde:-chromotropic acid. The mixture was reacted with stirring in a stoppered flask at room temperature for 1 week. The resulting dark red solution (70 ml) was filtered under vacuum, and the filtrate, after being concentrated was precipitated by adding 200 ml of acetonitrile. The precipitated product was collected by filtration and taken to dryness under vacuum. The yield of KY-1 was 95%. The compound was characterized as follows:

Melting point (M.P.)>300° C.;

HPLC in $CH_3CN/MeOH/H_2O/TFA$: 14'48" single peak;

(IR/KBr)=3425 (OH), 1638 (Ar), 1181, 1044 ($SO_3$) $cm^{-1}$;

UV ($H_2O$): 238.0, 358.5 nm

Mol Weight: 1505 (M+1) by mass spectroscopy;

$H^1$NMR($CD_3OD$), chemical shifts on the $\gamma$ scale: 5.20 ($CH_2$, 8.01 (ArH) ppm;

$C^{14}$ NMR ($D_2O$), chemical shifts on the $\gamma$ scale: 27.19, 120.18, 121.69, 122-06, 122-67, 133-30, 142.97, and 154.42 ppm.

Analysis: ($C_{11}H_6O_8S_2Na_2$)$_4$—$6H_2O$ or ($C_{11}H_6O_8S_2Na_2$)$_8$—$6H_2O$ Found: C 33.17, H 2.54, Na 11.93;

Calculated: C 32.75, H 2.23, Na 11.41.

B. KY-3 ($R_1$=OH, $R_2$=$SO_2NH_2$, $R_3$=H, $R_4$=—$CH_2$—)

KY-1 (2 mM) was treated with 5 ml chlorosulfonic acid and the mixture was stirred at room temperature for one-half hour. DMSO (10 ml) was added slowly to the mixture which was subsequently stirred at 80° C. for 1 hour. The resultant mixture was added with 100 ml acetonitrile to precipitate the product which was collected by filtration and then washed with ether.

The crude product was dissolved in 100 ml of 25% ammonium water solution and allowed to react for 2 hours at room temperature. The mixture was concentrated in vacuo and the remaining oil was dissolved in a small amount of water and filtered. The product was precipitated by adding acetonitrile to the filtrate and collected by filtration and washing with acetonitrile. The compound was characterized as follows:

Melting point (M.P.)>300° C.;

Mass spec: 1452 (M-$7NH_2$);.

HPLC in $CH_2CN/MeOH/H_2O/TFA$: 11'46" single peak;

(IR/KBr) =3430 (OH), 3187, 1686 ($NH_2$), 1637 (Ar), 1211, 1110, 1044 ($SO_3$) $cm^{-1}$;

UV ($H_2O$): 246 nm;

$H^1$ NMR($D_2O$), chemical shifts on the $\gamma$ scale: 5.15 ($CH_2$), 7.5-8.2 (ArH) ppm;

Analysis: ($C_{44}H_{40}O_{26}S_{10}Na$)—$4H_2O$

Found: C 28.62, H 3.93, N 8.82, S 17.17, Na 5.44;

Calculated: C 28.51, H 3.89, N 9.07, S 17.28, Na 4.97.

C. KY-42 ($R_1$=OH, $R_2$=$SO_3Na$, $R_3$=H, $R_4$=>CHCOOH)

Chromotropic acid, disodium (10 mM) in 50 ml water was mixed with glyoxylic acid (10.0 mM, in 5 ml water) and 10 ml of 37% hydrogen chloride at room temperature. The mixture was boiled for 8 hours and the color of the solution turned to dark red. The resultant solution was added to 50 ml of water and filtered. The filtrate was concentrated and ethanol was added to precipitate the product of KY-42. The yield was 87%. The compound was characterized as follows:

Melting point (M.P.)>300° C.;
Mass spec: 1623 (M-3H$_2$O).
HPLC in CH$_3$CN/MeOH/H$_2$O/TFA: 10'36" single peak;
(IR/KBr) =3452 (OH), 1801, 1719 (Co), 1638 (Ar), 1206, 1050 (SO$_3$) cm$^{-1}$;
UV (H$_2$O): 238.0, 351.5, 520 nm;
H$^1$ NMR(D$_2$O), chemical shifts on the $\gamma$ scale: 7.10 (CHCO$_2$H) 8.00 (ArH) ppm;
$\overline{C}^{14}$ NMR (D$_2$O), chemical shifts on the $\gamma$ scale: 116.04, 118.90, 120.94, 121.27, 122.30, 124.30, 124.68, 126.60, 128.37, 136.48, 136.71, 140.50, 143.93, 144.26, 145.75, 152.01, 154.33, 156.01, 156.67;
Analysis: (C$_{12}$H$_6$O$_{10}$S$_2$Na$_2$)$_4$—H$_2$O
(Found: C 32.74, H 2.50;
Calculated: C 32.88, H 1.83.

D. KY-123 ($R_1$=OH, $R_2$=$SO_2H$, $R_3$=H, $R_4$=—CH$_2$—)

KY-1 (2 mM) was treated with 5 ml chlorosulfonic acid and the mixture was stirred at room temperature for one-half hour. DMSO (10 ml) was added slowly to the mixture which was subsequently stirred at 80° C. for 1 hour. The resultant mixture was added with 100 ml acetonitrile to precipitate the product which was collected by filtration and then washed with ether. The crude sulfonyl chloride product was treated with sodium sulfite (20 mM) in 4 ml water. The reaction mixture was kept slightly alkaline by addition at intervals of small portions of 50% NaOH for 2 days. After solvent removal, ethanol was added to precipitate the product, which was acidified by addition of 50% H$_2$SO$_4$, followed by addition of ethanol to precipitate sodium sulfate. The ethanol phase was mixed with ether (1:2, v/v) to precipitate the desired product. Product yield was 39%.

E. KY-147 ($R_1$=OH, $R_2$=$SO_2NHCH_3$, $R_3$=H, $R_4$=—CH$_2$—).

N-methylchromotropic acid chloride was formed by reacting chromotropic acid (disodium salt) with sulphonylchloride in the presence of DMF. The reaction was carried out with stirring at 80° C. for 4 hours. After removal of solvent and excess of thionylchloride in vacuo, acetonitrile was added to precipitate the chromotropic acid chloride which was subsequently collected by filtration and washed with ether. The crude product was added to 20 ml of methylamine and stirred for 2 hours. After removal of all solvent from the resultant substance, the residue was dissolved in a 200 ml of cold methanol and filtered. The filtrate was added with acetonitrile to precipitate the product-N-methylchromotropic acid. Yield 56%.

N-methylchromotropic acid (2 mM) in 3 ml water was reacted with 37% formaldehyde (1 ml) at room temperature for one week. Acetonitrile was added to precipitate the product which was collected by filtration and washed by acetonitrile. Yield was 85%.

F. KY-151 ($R_1$=OCH$_3$, $R_2$=$SO_3Na$, $R_3$=H, $R_4$=—CH—).

Chromotropic acid, disodium (50 mM) was dissolved in 80 ml of NaOH water solution (0.2M NaOH) and heated to 50° C., dimethylsulfate (0.2M) was added slowly for 1 hour. The mixture was continuously stirred for another 2 hours and left at room temperature for 2 days. Saturated NaCl solution (100 ml) was added to the resultant substance and filtered. The precipitate was washed with ethanol, acetonitrile and ether sequentially. The dry substance was dissolved in 100 ml of methanol and filtered. The filtrate was concentrated and ether was added to precipitate the dimethyl ether of chromotropic acid, disodium. The yield of the dimethylether of chromotropic acid was 71%.

Dimethylether of chromotropic acid, disodium (2.3 mM) dissolved in 5 ml DMF was treated with treated with 1 g para-formaldehyde in the presence of acetic acid (15 ml) at 80° C. for 12 hours. The product was precipitated and isolated as in Example 1A. The product yield was 32%.

G. KY-143 ($R_1$=OH, $R_2$=$SO_2Na$, $R_3$=H, $R_4$=—H—).

Chromotropic acid (3 mM) in 5 ml DMF was treated with 3 ml of thionylchloride at 80° C. for 4 hours. After removal of solvent and excess thionylchloride in vacuo, acetonitrile was added to precipitate the chromotropic acid chloride which was subsequently collected by filtration and washed with ether. The crude product was added to a solution containing 6 g anhydrous sodium sulfate, 4.2 g sodium bicarbonate in 24 ml H$_2$O at 70°-80° C. When addition was complete, the mixture was heated and stirred at 80° C. for 1 hour, then stored overnight at room temperature. After removal of all the solvent, 200 ml methanol was added to precipitate the crude product, which was then treated with HCl solution at room temperature. Acetonitrile was added to precipitate the crude product. The latter was treated with 37% formaldehyde at room temperature under nitrogen for 1 week. Product yield was 38%.

H. KY-158 ($R_1$=OH, $R_2$=$SO_2CH_3$, $R_3$=H, $R_4$=—CH—).

KY-1 from Example 1A was first treated with thionyl chloride to produce chromotropic acid sulfonyl chloride. This compound was reduced by excess sodium sulfite in the presence of sodium bicarbonate to produce the corresponding sodium sulfonate salt of chromotropic acid ($R_2$=$SO_2Na$). The sulfonate salt was treated with sulfonyl chloride to produce the sulfonyl chloride. The product was dissolved in methanol and treated with sodium methoxide in methanol under nitrogen. The product was worked up as described in Example 1A. Product yield was about 21%.

I. KY-175 ($R_1$=OH, $R_2$=$SO_3CH_3$, $R_3$=H, $R_4$=—CH$_2$—).

KY-1 from example 1A was first treated with thionyl chloride to produce chromotropic acid sulfonyl chloride. This compound was then treated with sodium methoxide in methanol in the presence of sodium salt. The product was worked up as described in Example 1A. Product yield was about 29%.

J. KY-270 ($R_1$=OCOCH$_3$, $R_2$=SO$_3$Na, $R_3$=H, $R_4$=—CH—).

KY-1 from Example 1A (0.66 mmole) was dissolved in 3 ml water containing 0.1 g NaOH. To this was added 1 g acetic chloride (13 mmole) and the reaction was allowed to proceed at room temperature overnight with stirring. After solvent removal, 25 ml ethanol was added to precipitate the product. The crude product was dissolved in methanol and filtered The filtrate was allowed to precipitate, giving a 87% yield.

K. KY-346 ($R_1$=OH, $R_2$=SO$_3$Na, $R_3$=H, $R_4$=—CH$_2$—N(CH$_3$)—CH$_2$—)

Chromotropic acid disodium salt, was dissolved in 80 ml of water at a concentration of 50 mM with stirring at 50° C. until the solution turned to clear, hexamethylenetetramine (50 mM) was then added to above solution with continuous stirring at the same temperature for additional two hours. At this time, the color of this mixture converted to dark blue. The mixture was allowed to stir at room temperature for 2 days. The resultant dark blue solution was filtered and the filtrate was concentrated, evaporated by flask, which was subsequently treated with 200 ml methanol to precipitate the product KY-346. The yield of KY-346 was 85%. The compound was characterized as follows:

M.P.>300° C.;
HPLC in CH$_3$CN/MeOH/H$_2$O/TFA: 13'07" single peak;
(IR/KBr) =3425 (OH), 1626 (Ar), 1197, 1052 (SO$_3$) cm$^{-1}$;
UV (H$_2$O): 232.0, 377.5 nm
Analysis: (C$_{13}$H$_{11}$O$_8$S$_2$Na$_2$)$_4$—6H$_2$O
Found: C 33.17, H 2.13, N 2.75, Na 11.51,
Calculated: C 37.23, H 2.63, N 3.34, Na 10.98.
Molecular weight: 1656 by gel filtration.

EXAMPLE 2

Cytotoxicity in Proliferating Cells

A panel of human cell lines was used to check the toxicity of the drugs, including: KB (nasopharyngeal carcinoma), HeLaS$_3$ (cervical epithelial carcinoma), PLC (hepatocarcinoma), HepG$_2$ (human hepatocarcinoma) HepG$_2$T$_{14}$ (hepatocarcinoma transfected with HBV), WI38 (normal human lung fibroblast), BT549 (breast cancer), SW480 (breast cancer), and A549 (lung cancer).

$5 \times 10^4$ cells were plated in each well of a 24 well multi-dish in 1 ml of RPMI-1640 containing 5% FCS and P/S. On the second day after plating, one of the thirty test compounds given in Table 1 below was added to the cells, at concentrations between 1–100 µg/ml. Three days later, the medium was removed and the cells were stained with Commassie Blue in 40% methanol and 10% acetic acid. The results are discussed in Section II above.

EXAMPLE 3

Inhibition of HSV Activity: Cytopathic Effect

Vero cells were maintained in RPMI-1640 medium supplemented with 5% fetal calf serum, 100 Units of penicillin per ml and 100 µg of streptomycin per ml at 37° C., in a humidified incubator containing 7% CO$_2$. The HSV strains HSV-1 (Kos-1) and HSV-2 (333) were used.

$1 \times 10^5$ Vero cells were plated in each well of a 96 well microtitre plate in 0.2 ml RPMI-1640 medium containing 5% FCS and 0.1% methyl cellulose (15 cps). After overnight incubation, and cell doubling, the medium was aspirated and replaced with 100 µl of the same medium containing 2% FCS, and 50 µl control or drug solution to a final drug concentration of 10 µg/ml and 50 µl virus, containing about 3 PFU/cell, i.e., $6 \times 10^5$ PFU/well, of HSV-1 or HSV-2.

The cells were cultured for 24 hours at 37° C., at which time cytopathic effects are clearly visible. In the absence of viral infection, the cells form an even monolayer of fibroblast cells. With viral infection, the cells form a suspension of round cells, followed by cell clumping, whose appearance is easily distinguishable from normal fibroblast cells. If no detectable cytopathic effect was produced, the test was repeated with 20 µg/ml. A parallel set of cells without virus inoculation were done as a control for cytotoxicity to Vero cells.

Table 1 above shows the structures of the compounds which were tested, and Table 2, column 2, the compounds which protected the cells from cytopathic effect (+).

EXAMPLE 4

Inhibition of HSV Activity: Plaque Reduction

Vero cells were maintained in RPMI-1640 medium supplemented with 5% fetal calf serum, as in Example 3. $4 \times 10^5$ Vero cells were plated in a 24-well plate, in 1 ml RPMI-1640 medium containing 5% FCS and 0.1% methyl cellulose (15 cps). After overnight incubation, and cell doubling, the medium was aspirated and replaced with 100 µl of the same medium containing 2% FCS, which contained 50 µl control or drug solution to a final drug concentration of 10 µg/ml and 50 µl virus, containing about 3 PFU/cell, i.e., $2.4 \times 10^6$ PFU/well, of HSV-1 or HSV-2, as in Example 3.

After 2 hrs. at 37° absorption the virus and the drugs were removed and the cells were washed with PBS and 0.5 ml of 1% methylcellulose (4K cps) in RPMI-1640 +2% FCS +penicillin/streptomycin (P/S) was added. Two days later, the media were removed. The cells were stained with 0.8% crystal violet in 50% ethanol. The plaques formed were counted and the percentage of inhibition was calculated by dividing by the plaques formed in control. ED$_{50}$ values, indicating the concentration of drug needed produce 50% inhibition of viral plaques, were calculated assuming a linear dose response for viral plaque inhibition. The calculated ED$_{50}$ values are given in Table 2 above.

EXAMPLE 5

Inhibition of HSV Activity: Viral Yield Inhibition $1 \times 10^6$ HeLa S$_3$ were plated in 25 T flasks in 5 ml RPMI-1640 +5% FCS +P/S. 24 hours later, the medium was aspirated and replaced with $6 \times 10^6$ PFU HSV-1 or HSV-2, and serial dilutions of selected KY compounds, at 10, 5, 2.5, 1.25, and 0.625 µg/ml drug. After growth at 37° C. for 24 hours in 2 ml of RPMI-1640 containing 2% FCS and P/S, the cells were frozen at −70° C. until the time for titration. The cells were freeze/thawed 3 times to release virus from the cells, and serially diluted 10 fold.

$1 \times 10^5$ Vero cells were plated in each well of 24 well multi-dish in 1 ml RPMI-1640+5% FCS +P/S +0.1% methylcellulose (15 cps). On the second day, after removal of the medium, the 10 fold serially diluted virus in 100 µl was added in duplicate. After 2 hours incubation at 37° C., the virus was removed and 0.5 ml methylcellulose (4K cps) in RPMI-1640 and 2% FCS +P/S was added. Two days later, the medium was removed. The cells were stained in 0.8% crystal violet in 50% ethanol. The plaques formed were counted and the titer was calculated from the fold of dilutions.

The reduction in virus yield, as a function of KY compound concentration, is seen in FIGS. 3A-3E for five of the KY compounds tested.

EXAMPLE 6

Activity Against Drug-Resistant Strains of HSV-1 and HSV-2

The following strains of HSV-1 and HSV-2 virus were used: KOS, a wild type HSV-1 virus; KOS (PMEA) and KOS (PFA), both drug-resistant HSV-1 viruses having a DNA polymerase mutation; 333, a wild type HSV-2 HSV-2 virus, and 333 (DHPG), a drug-resistant HSV-2 virus having a thymidine kinase mutation.

Inhibition of viral yield was by KY-1, acyclovir (ACV), DHPG, PFA, and PMEA was examined in each of the five HSV strains substantially as described in Example 5. Briefly, Hela $S_3$ were plated in 25 T flasks in culture, and 24 hours later, the medium was aspirated and replaced with $6 \times 10^6$ PFU of the selected HSV strain, and serial dilutions of KY-1, ACV, DHGP, PFA, and PMEA. After growth at 37° C. for 24 hours in 2 ml of RPMT-1640 containing 2% FCS and P/S, the cells were frozen at −70° C. until the time for titration. The cells were freeze/thawed 3 times to release virus from the cells, serially diluted 10 fold, and the serial dilutions were added to Vero cells in culture. After 2 hours incubation at 37° C. the virus was removed and 0.5 ml methylcellulose (4K cps) in RPMI-1640 and 2% FCS +P/S was added. Two days later, the medium was removed. The cells were stained in 0.8% crystal violet in 50% ethanol. The plaques formed were counted and the titer was calculated from the fold of dilutions. From the drug dose response, the concentration of each drug required to effect a 90% inhibition of virus yield, the $IC_{90}$ concentration was determined. These values are shown in Table 3 above.

EXAMPLE 7

Inhibition of HSV-1 Binding to Vero Cells

Vero cells were maintained in RPMI-1640 medium, as described in Example 3. After overnight incubation, and cell doubling, the medium was aspirated and replaced with 100 μl of medium containing 2% FCS composed of 50 μl control or drug solution to a final drug concentration of 10 μg/ml and 50 μl virus, containing about 3 PFU/cell, i.e., $6 \times 10^5$ PFU/well, of $H^3$-labeled HSV-1. At time intervals of 5, 30, 60, 120, and 240 minutes, cells were removed from the suspension, washed two times with PBS, and assayed for bound virus (cpm $^3H$). The results are given in FIG. 4, where the control virus binding is indicated by solid circles, and the drug-inhibited binding, by open rectangles.

EXAMPLE 8

Effect of Drug/Virus Exposure on HSV Inhibition

Vero cells were maintained in RPMI-1640 medium, as above. After overnight incubation, and cell doubling, the medium was aspirated and replaced with 100 μl of medium containing 2% FCS. In one group of wells, serial dilutions of KY-1 compound, between 0.625 and 10 μg/ml drug were added in 50 μl together with 50 μl of HSV-1 virus suspension, $5 \times 10^6$ PFU per well. The cells were incubated for 2 hours at 37° C., then washed with PBS and assayed for number of virus plaques, as in Example 4.

In a second group of cells, serial dilutions of the drug were added to the cells, prior to the addition of the HSV-1 virus, and the cells were incubated for 2 hours at 37° C. in the presence of the virus. After washing the cells to remove free drug, virus suspension was added, $5 \times 10^6$ PFU per well. The cells were incubated for 2 hours at 37° C., then washed with PBS and assayed for number of virus plaques, as in Example 4.

In a third group of cells, 100 μl virus suspension was added to the cells, $5 \times 10^6$ PFU per well, and the cells were incubated for 2 hours at 37° C., then washed with PBS to remove unbound virus. Serial dilutions of KY-1 compound, between 0.625 and 10 μg/ml drug were added to the cells in 100 μl. The cells were incubated for 2 hours at 37° C. in the presence of the drug, then washed with PBS and assayed for number of virus plaques, as above.

Figure 5:
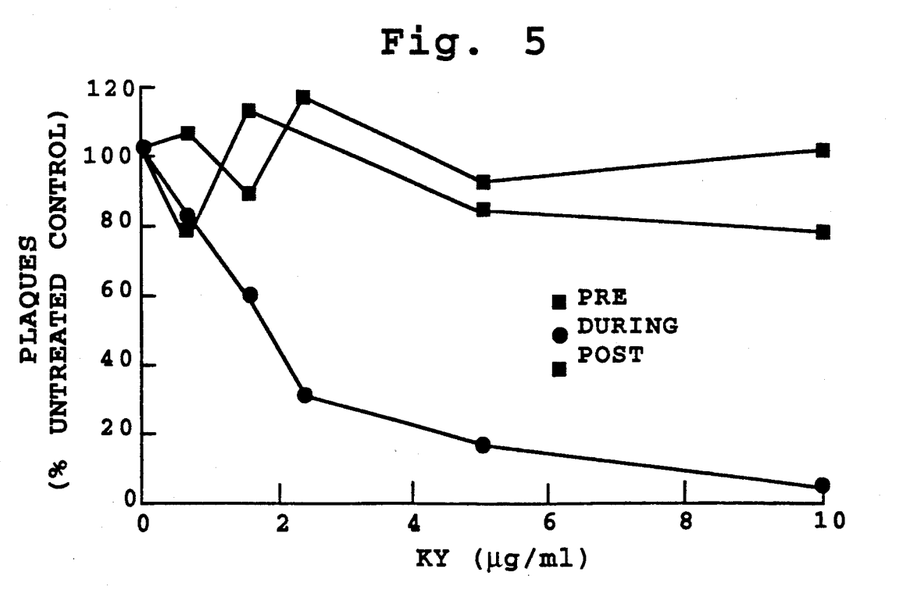
FIG. 5 is a plot of the inhibition in plaque formation of HSV-1 virus when the virus is exposed to the compound KY-1 before (open squares), (ii) after (closed squares), and during (closed circles) incubation with Vero cells.

The numbers of plaques observed in each of the above treatment methods, expressed as percent of untreated control, are plotted in FIG. 5. The solid circles indicate co-exposure of the cells to drug and virus; the solid squares, preincubation of the cells with drug before addition of virus; and the open squares, preincubation of the cells with virus before addition of drug.

EXAMPLE 9

Inactivation of HSV-1 by KY compounds

Purified HSV-1 was suspended in PRMI-1640 containing 2% FCS and P/S. To aliquots of the suspensions were added control, KY-1, or KY-217 solution, to a final drug concentration of 10 μg/ml, and a final virus particle concentration of $6 \times 10^6$ or $6 \times 10^5$ PFU/ml The suspensions were incubated for 1 hour at 37° C., then diluted serially at 10 fold dilutions to final drug concentrations of 10, $10^0$, $10^{-1}$, $10^{-2}$, $10^{-3}$, and $10^{-4}$ μg/ml drug concentrations. The serially diluted particles were then added to Vero cells for two hours, as in Example 4, and the cells examined for plaques 48 hours later. The number of plaques counted on each of two plates, for each virus and drug concentration, are given in Table 4.

EXAMPLE 10

Binding of KY Compounds to HSV Proteins

A. Binding of KY compound to HSV Proteins

HSV-1 and HSV-2 viral suspensions from above, each at a concentration of about $5 \times 10^7$ CFU/ml, were incubated for 2 hours at 37° C. with $5 \times 10^5$ cpm $^{14}C$-labeled KY-1 (50 μg/ml). Each viral suspension was divided into two aliquots and solubilized with 0.5% sodium dodecyl sulfate (SDS), with or without 1% mercaptoethanol. The four solubilized samples were fractionated on 8.5% polyacrylamide gel, and the gels developed by autoradiography, according to standard procedures. The autoradiographs of the four samples are seen in FIG. 6, where the lanes are HSV-1, with (lane A) and without (lane B) mercaptoethanol, and HSV-2, with (lane D) and without (lane E) mercaptoethanol, with the marker proteins in lane C.

B. Identification of Binding Proteins

HSV-1 and HSV-2 virus suspensions were solubilized with SDS and fractionated on SDS-PAGE as above. Each sample was run in triplicate, corresponding to groups D, B, and C in FIG. 7. The two gels in each group were analyzed by Western blotting as follows: The gels in groups D, B, and C were first reacted with mouse monoclonal antibody specific against HSV glycoprotein gD, gB, and dC, respectively. The antibodies were obtained from Dr. S. Chatterjee from the University of Alabama. The gels were then incubated with alkaline phosphatase-labeled goat anti-mouse antibody, to label the glycoprotein in each group. The glycoprotein with bound antibody was identified by reaction with $H_2O_2$ in the presence of nitroblue tetrazolium and bromochloroindolephosphate, according to standard methods. The results are shown in FIG. 7.

EXAMPLE 11

Bioavailability after Topical Administration

A New Zealand rabbit was given a topical administration of $^{14}C$-labeled KY-1 compound at the vaginal orifice. At time periods 1, 2, 4, 6, 8, 10, 12, 16, 20, and 24 hours, the amount of label present in a given volume of serum, and at the vaginal orifice of the animal were measured. The results are shown in FIGS. 8A and 8B, respectively, where the drug concentrations have been corrected to ng/ml units for drug in the bloodstream and μg/ml units for drug measured at the vaginal orifice.

EXAMPLE 12

Effect of KY Topical Administration on Genital HSV Infection

A. Virus and Viral Inoculation

The MS strain of HSV-2 was utilized for the experimental animal infection. Female Hartley strain guinea pigs (Charles River Breeding Laboratories, Kingston, N.Y.) weighing 250–300 g were inoculated intravaginally with $2.0 \times 10^5$ plaque-forming units of HSV-2 one hour after being swabbed for removal of vaginal secretions.

B. Treatment of Guinea Pigs

Groups of 10 guinea pigs were treated topically (0.1 ml intravaginally +0.1 ml on external genital skin) three times daily (approximately every eight hours) for seven days beginning 6h or 48h after inoculation with HSV-2. Groups of three uninfected animals were treated in a similar manner to assess any skin irritation.

C. Sample Collection and Virus Assays

To determine the effect of treatment on vaginal viral replication, swabs of vaginal secretions were obtained on days 1, 3, 5, 7 and 10 after HSV inoculation, placed in a tube containing 2.0 ml of media, vortexed and frozen at −70° C. until titrated for HSV-2. When all samples were collected, they were thawed, diluted serially and HSV-2 titers determined using rabbit kidney cells in a microtiter CPE assay.

D. Evaluation of Efficacy

To determine the effect of therapy on the development and spread of external genital lesions, lesion severity was scored on a 0-5+ scale through the primary infection (21 days). Lesion score-day areas and virus titer-day areas under the curve, and peak lesion scores and peak virus titers between untreated and placebo-treated or placebo-treated and drug-treated animals were compared using the Mann-Whitney U rang sum test. A p-value of 0.05 or less was considered significant. The results are discussed with reference to Tables 10 and 11 in Section V above.

Although the invention has been described with reference to specific drug compounds, methods of synthesis, and treatment methods, it will be appreciated that modification and changes may be made without departing from the invention.

It is claimed:

1. A method of inhibiting cell infection in a mammalian subject by herpes simplex virus-1 or herpes simplex virus-2 (HSV), comprising
   administering to the subject a pharmaceutically effective dose of a macrocyclic chromotropic acid compound effective to inhibit binding of HSV to HSV-infectable cells.

2. The method of claim 1, wherein the compound has the form:

where
   $R_1$ is a polar, hydrogen accepting substituent,
   $R_2$ is a sulfonate, a sulfinate, sulfonyl, or a sulfonamide radical,
   $R_3$ is —H or an uncharged or negatively charged substituent with a log (octanol/water partition coefficient) value less than 1, and
   $R_4$ is a 1 to 3 atom-chain bridge linking each naphthalene group through a naphthalene-ring carbon-methylene linkage.

3. The method of claim 2, wherein $R_3$ is —H.

4. The method of claim 2, wherein $R_4$ is a methylene bridge.

5. A method of inhibiting cell infection by herpes simplex virus-1 or herpes simplex virus-2 (HSV) in a mammalian subject, comprising
   administering to the subject a macrocyclic chromotropic acid compound effective to bind selectively to HSV proteins, as evidenced by protein-specific binding of the compounds to HSV proteins fractionated by sodium dodecyl sulfate polyacrylamide gel electrophoresis, in a pharmaceutically effective dose.

6. The method of claim 5, wherein the compound has the form:

where
- $R_1$ is a polar, hydrogen accepting substituent,
- $R_2$ is a sulfonate, sulfinate, sulfonyl, or a sulfonamide radical,
- $R_3$ is —H or an uncharged or negatively charged substituent with a log(octanol/water partition coefficient) value less than 1, and
- $R_4$ is a 1 to 3 atom-chain bridge linking each naphthalene group through a naphthalene-ring carbon-methylene linkage.

7. A method of inhibiting cell infection by herpes simplex virus-1 or herpes simplex virus-2 (HSV) in a mammalian subject, comprising
administering to the subject a pharmaceutically effective dose of a macrocyclic chromotropic acid compound having the form:

where
- $R_1$ is a polar, hydrogen accepting substituent,
- $R_2$ is a sulfonate, sulfinate, a sulfonyl, or a sulfonamide radical,
- $R_3$ is —H or an uncharged or negatively charged substituent with a log (octanol/water partition coefficient) less than 1, and
- $R_4$ is a 1 to 3 atom-chain bridge linking each naphthalene group through a naphthalene-ring carbon-methylene linkage, and
- the compound is effective to bind selectively to HSV proteins, as evidenced by protein-specific binding of the compounds to HSV proteins fractionated by sodium dodecyl sulfate polyacrylamide gel electrophoresis.

8. A method of inhibiting cell infection by herpes simplex virus-1 or herpes simplex virus-2 (HSV) in a mammalian subject, comprising
administering to the subject a pharmaceutically effective dose of a macrocyclic chromotropic acid compound having the form:

where
- $R_1$ is a polar, hydrogen accepting substituent,
- $R_2$ is a sulfonate, a sulfinate, a sulfonyl, or a sulfonamide radical,
- $R_3$ is —H or an uncharged or negatively charged substituent with a log(octanol/water partition coefficient) value less than 1, and
- $R_4$ is a 1 to 3 atom-chain bridge linking each naphthalene group through a naphthalene-ring carbon-methylene linkage, and
- the compound is effective to inhibit binding of HSV to HSV-infectable cells.

* * * * *